United States Patent
Nyholm et al.

(10) Patent No.: US 8,382,701 B2
(45) Date of Patent: Feb. 26, 2013

(54) METHOD FOR ENSURING CONSTANT SPEED OF A MOTOR IN AN INJECTION DEVICE

(75) Inventors: Kim Nyholm, Snekkersten (DK); Bo Vestergård Jensen, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/174,867

(22) Filed: Jul. 1, 2011

(65) Prior Publication Data

US 2011/0264046 A1   Oct. 27, 2011

Related U.S. Application Data

(62) Division of application No. 11/816,442, filed as application No. PCT/DK2006/000025 on Jan. 17, 2006, now Pat. No. 7,993,300.

(60) Provisional application No. 60/655,797, filed on Feb. 24, 2005.

(30) Foreign Application Priority Data

Feb. 21, 2005   (DK) ................................ 2005 00260

(51) Int. Cl.
 *A61M 31/00*   (2006.01)
(52) U.S. Cl. ...... 604/67; 604/151; 604/154; 318/400.14
(58) Field of Classification Search ............. 318/400.01, 318/400.14, 696, 721, 799, 560, 568.18, 318/779, 280; 604/154, 67, 151
See application file for complete search history.

(56) References Cited

U.S. PATENT DOCUMENTS

| | | | |
|---|---|---|---|
| 3,812,843 A | 5/1974 | Wootten et al. | |
| 4,563,175 A | 1/1986 | LaFond | |
| 4,722,734 A | 2/1988 | Kolln | |
| 4,838,857 A | 6/1989 | Strowe et al. | |
| 5,505,697 A | 4/1996 | McKinnon, Jr. et al. | |
| 5,690,618 A * | 11/1997 | Smith et al. ................... | 604/232 |
| 5,928,197 A * | 7/1999 | Niehoff ......................... | 604/155 |
| 5,993,412 A | 11/1999 | Deily et al. | |
| 6,259,587 B1 | 7/2001 | Sheldon et al. | |
| 6,340,357 B1 | 1/2002 | Poulsen et al. | |
| 6,520,930 B2 * | 2/2003 | Critchlow et al. .............. | 604/67 |
| 6,544,229 B1 | 4/2003 | Danby et al. | |
| 6,945,954 B2 * | 9/2005 | Hochman et al. ............... | 604/67 |
| 7,128,729 B2 * | 10/2006 | Duchon et al. ................. | 604/154 |
| 2002/0052575 A1 * | 5/2002 | Hochman ....................... | 604/151 |
| 2003/0014013 A1 | 1/2003 | Choi | |
| 2004/0054328 A1 * | 3/2004 | Langley et al. ................. | 604/151 |

FOREIGN PATENT DOCUMENTS

| | | |
|---|---|---|
| EP | 0293958 | 12/1988 |
| EP | 0364010 B1 | 4/1990 |
| EP | 1323441 A2 | 7/2003 |

* cited by examiner

*Primary Examiner* — Antony M Paul
(74) *Attorney, Agent, or Firm* — Wesley A. Nicolas; Marc A. Began; Reza Green

(57) ABSTRACT

The present invention relates to a method for ensuring a constant target speed of a battery driven electrical motor, the battery driven electrical motor being adapted to move a piston rod in an injection device so as to inject a set dose of medicine from the injection device, the method comprising the steps of setting a first target speed to be reached by the motor, determining whether the first target speed can be reached, and, if the first target speed can be reached, maintaining the first target speed until a set dose of medicine has been injected from the injection device, or if the first target speed cannot been reached, setting a second target speed.

4 Claims, 1 Drawing Sheet

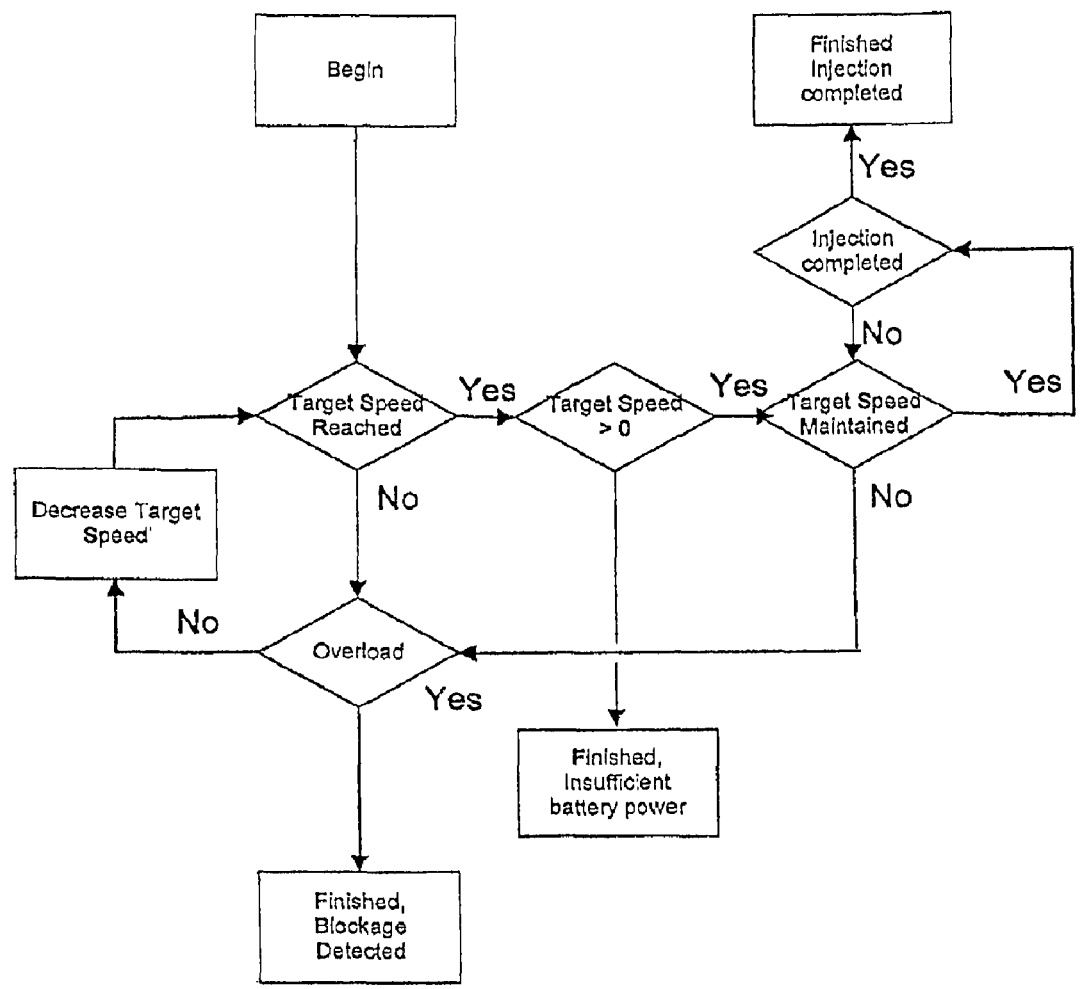

METHOD FOR ENSURING CONSTANT SPEED OF A MOTOR IN AN INJECTION DEVICE

CROSS-REFERENCE TO RELATED APPLICATIONS

This application is a divisional application of U.S. application Ser. No. 11/816,442, filed Aug. 16, 2007, which is a 35 U.S.C. §371 national stage application of International Patent Application PCT/DK2006/000025 (published as WO 2006/086980 A1), filed Jan. 17, 2006, which claims priority of Danish Patent Application PA 2005 00260, filed Feb. 21, 2005; and which further claims priority under 35 U.S.C. §119 of U.S. Provisional Application 60/655,797, filed Feb. 24, 2005.

FIELD OF THE INVENTION

The present invention relates to a method for ensuring constant speed of a battery driven motor in an injection device. In particular, the present invention relates to a method for setting a preferred target and reducing this preferred target speed to secondary target speed if the capacity of the battery is insufficient to reach or maintain the preferred target speed. The present invention further relates to a method for generating an alarm signal if the target speed cannot be reached or maintained.

BACKGROUND OF THE INVENTION

U.S. Pat. No. 5,505,697 discloses an electrically powered jet injector impacting a plunger driver against a plunger to generate a high initial pressure pulse for piercing the skin of a human. The plunger driver then continues to generate a lower delivery pressure until an injection of for example insulin is completed. A microprocessor within the injector controls the speed and direction of the electric motor which moves the plunger driver. The injector provides a subcutaneous injection especially useful for injecting insulin to treat diabetes.

U.S. Pat. No. 5,505,697 discloses that during the initial pierce phase of the injection, there is a very fast pressure rise to a peak pressure of about 4,000 psi. This peak pressure serves to pierce the skin and generate a short, slightly elongated channel in the sub-cutaneous tissue. At about the time the initial pressure peak is reached, a CPU provides new commands to a power switching circuit board so as to reduce the motor speed in order to deliver a steady state delivery pressure during the delivery phase. The delivery pressure is typically between about ½ and ⅓ of the peak pressure achieved. High pressures are necessary only for a very short duration, to pierce the skin and make a nominal channel into the underlying tissue. Then, the following low, steady delivery pressure only fills the existing channel with fluid, without further tissue disruption. Control of pressure in the delivery phase is provided by closed loop regulation of the motor speed. Specifically, pulse width modulation (PWM) is used, wherein the "on-time" of a fixed frequency pulse generator in the CPU is varied to modulate the average current provided to the motor. The closed loop control allows the device to compensate for variations in battery voltage, friction due to wear or environment temperature changes, or variations in ampoule parameters, especially plunger friction.

There is in U.S. Pat. No. 5,505,697 no mentioning of how to compensate for variations in the battery voltage. Thus, there is in U.S. Pat. No. 5,505,697 no mentioning of how the speed of the motor is kept constant is situations where the battery voltage decreases to levels below the nominal voltage level of the battery. Hence, there is a need for a method for ensuring that the motor speed can be kept constant even in situations wherein the battery voltage falls below the nominal voltage level of the battery.

It is an object of the present invention to provide a method for ensuring constant speed of a battery driven motor in an injection device.

It is a further object of the present invention to provide a method for ensuring constant speed of a battery driven motor in situations where the battery voltage is lower than the nominal voltage of the battery.

SUMMARY OF THE INVENTION

The above-mentioned objects are applied with by providing, in a first aspect, a method for ensuring a constant target speed of a battery driven electrical motor, the battery driven electrical motor being adapted to move a piston rod in an injection device so as to inject a set dose of medicine from the injection device, the method comprising the steps of
  setting a first target speed to be reached by the piston rod,
  determining whether the first target speed can be reached, and,
  if the first target speed can be reached, maintaining the first target speed until the set dose of medicine has been injected from the injection device, or
  if the first target speed cannot been reached, setting a second target speed.

The method according to the present invention may further comprise the steps of determining whether the second target speed can be reached, and
  if the second target speed can be reached, maintaining the second target speed until the set dose of medicine has been injected from the injection device, or
  if the second target speed cannot be reached, setting a third target speed.

The method according to the present invention may even further comprise the steps of determining whether the third target speed can be reached, and, if the third target speed can be reached, maintaining the third target speed until the set dose of medicine has been injected from the injection device, or, if the third target speed cannot been reached, shutting down the motor. By shutting down the motor is meant that the target speed is set to zero.

The first target speed may be higher than a second target speed which may be higher than a third target speed. Thus, at start up a control module of the injection device system sets the preferred target speed. If the preferred target speed cannot be reached a slightly lower target speed is set. In case this lower target speed cannot be reached an even lower target speed is set. This procedure may in principle be continued an arbitrary number of times, but since the user of the injection device within a reasonable period of time needs to know whether the injection device is capable of completing an injection of the set dose of medicine at a constant speed typically three target speeds are set before the motor is shut down and a warning signal is provided to the user of the injection device informing the user that the battery needs to be replaced.

The determining of the speed of the piston rod may comprise the step of measuring the speed of the motor using some sort of encoder unit and an associated electronic detector circuit. The method according to the present invention may further comprise the step of measuring the current provided to the motor. Such measurement may be performed by inserting a current sensor between the battery and the motor, or by measuring a voltage drop over an external resistor operatively connected to one of the terminals of the motor.

The method according to the present invention may further comprise the step of shutting down the motor if the current provided to the motor exceeds a predetermined value. High current can occur if the motor is somehow blocked, for example a mechanical blockage, or if the set dose is forced through a thin injection needle at high speed.

The method according to the present invention may further comprise the step of generating a battery alarm signal already when the second target speed is set. The battery alarm signal may be provided to a control module of the injection device so as to warn the user of the device that the capacity of the battery is insufficient to reach the first target speed.

In a second aspect, the present invention relates to a system for carrying out the method according to the first aspect of the present invention, the system comprising an electrical motor operatively coupled to a direction sensitive encoded unit, and a control module comprising a user interface, a microprocessor, a memory module, a motor controller and at least one A/D converter for converting an incoming analogue signal to the control module into a digital format.

The encoder unit may be directly connected to the motor shaft of a DC-motor so as to provide information regarding the angular position of the motor shaft and to provide information regarding the direction of rotation of the motor shaft. The user interface may in principle be any kind of user interface capable for supporting communication between the user of the injection device and the device. For example, push bottoms and pressure sensitive plat panel displays may be suitable user interfaces. The display may also provide information to the user regarding the status of the injection device. Also, alarm signals regarding the remaining capacity of the battery may be communicated to the user of the injection device via such flat panel display. The microprocessor may be an ASIC adapted to perform or carry out predetermined steps in order to control the reversing procedure of the piston rod. For example, the processing of signals, such as the measured current and the actual position of the piston rod may be handled by the microprocessor. The motor controller may comprise a conventional H-bridge comprising four transistor. Such H-bridge is capable of driving the motor in both a forward and a backward direction. The output voltage from the H-bridge may be varied by adjusting the duty circle of the pulse width modulated (PWM) control signal to one or more transistors. The A/D converter may be adapted to convert an analogue signal representing the current provided to the motor into a digital format for further processing.

In a third aspect, the present invention relates to an injection device for injecting a set dose of medicine from ampoule containing medicine, the injection device comprising a system according to the second aspect of the present invention. The medicine to be injected from the injection device may be insulin.

In a fourth aspect, the present invention relates to a computer program product adapted to carry out the method according to the first aspect of the present invention when said computer program product is run on a computer or microprocessor, such as an ASIC.

BRIEF DESCRIPTION OF THE DRAWING

The present invention will now be explained in further details with reference to FIG. 1 which depicts the method of the present invention in a flow chart form.

While the invention is susceptible to various modifications and alternative forms, specific embodiments have been shown by way of example in the drawing and will be described in details herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to a method for supplying power to a battery driven motor in an injection device, and ensuring that the motor is driven at a constant speed during injection of a set dose of medicine. Since the motor drives a piston rod which acts on an ampoule containing medicine it is highly essential that the piston rod is moved forward and towards the ampoule at a constant speed so that the medicine in the ampoule, such as for example insulin, is injected from the injection device at a constant volume per time unit.

When a set dose of medicine is to be injected from the injection device a control module sets a preferred target speed to be reached by the motor. During injection the speed of the motor and the current provided to the motor is regularly measured. If the motor can reach and maintain the preferred target speed the set dose is injection by driving the motor at this preferred motor speed until the injection is completed. If the preferred target speed cannot be reached due to a reduced voltage on the battery, or if the preferred target speed cannot be maintained, the control module sets a second target speed which is lower that the preferred target speed. At the same time a warning signal is generated telling the user of the injection device that the remaining capacity of the battery is insufficient to run the motor at the preferred target speed. Before the second target speed is set further attempts to reach the preferred target speed is initiated. Such attempts could involve an increase of the voltage level supplied to the motor. This increase is achieved by adjusting the PWM control signal to one or more transistors.

If the motor can reach and maintain this second target speed the set dose is injected at this motor speed. If the second target speed cannot be reached or maintained a third and even lower target speed is set by the control module. If the third target speed cannot be reached or maintained the control unit shuts down the motor and an alarm signal is generated telling the user that the battery needs to be replaced immediately.

One way of implementing the present invention is illustrated in the flow chart shown in FIG. 1. Starting at the box saying "Begin" the preferred target speed is set. After a predetermined period of time it is checked whether the motor has reached the preferred target speed. The motor speed is measured using an encoder operatively connected to the motor shaft of the motor. If the preferred is reached and can be maintained the injection is completed and the box "Finished injection completed" is reached, and the injection device is ready to inject a new dose of medicine.

If the preferred target speed cannot be reached it is checked whether the motor is overloaded or not. An overloading of the motor can for example be caused by a mechanical blockage of the motor shaft or a mechanical blockage of the piston rod driven by the motor. If such blockage is detected the motor is immediately shut down. An overloading situation of the motor is detected by measuring the current provided to the motor—if an overloading situation occurs the level of the current provided to the motor exceeds a predetermined value and the control module shuts down the motor.

If the motor cannot reach the preferred target speed, and no over current is detected, the target speed is decreased from the preferred target speed to a second and lower target speed. As already mentioned the motor has a predetermined period of time to reach the preferred target speed. This predetermined period of time may vary from a few sample rates to several sample rates. If a second target speed is set the motor must reach the second target speed within a time period corresponding to the time period given to reach the preferred target speed. If the second target speed can be reached and maintained the injection device completes the injection at the second target speed. If not a third and even lower target speed is set and the motor must reach this third target speed within a predetermined time period. If the third target speed can be reached and maintained the injected device completes the injection at the third target speed. If not, or if an over current is detected, the motor is shut down, and an error signal is generated. The error signal informs the user of the injection device that the battery needs to be replaced.

Typical ratios between the preferred target speed, the second target speed, and the third target speed are as follows: if the preferred target speed corresponds to 100%, the second and third target speed would typically correspond to 70% and 40%, respectively. However, other ratios as well as additional or fewer target speeds may also be applied.

The invention claimed is:

1. A system for ensuring a constant target speed of a battery driven electrical motor, the system comprising
 an electrical motor operatively coupled to a direction sensitive encoded unit, and
 a control module, wherein the control module sets a first target speed to be reached by the piston rod prior to beginning an injection, and,
  determines whether the first target speed can be reached, and
  if the first target speed can be reached, maintaining the first target speed until the set dose of medicine has been injected from the injection device, and
 if the first target speed cannot been reached, setting a second target speed,
  determining whether the second target speed can be reached, and,
  if the second target speed can be reached, maintaining the second target speed until the set dose of medicine has been injected from the injection device.

2. The system of claim 1, wherein the control module determines if the second target speed cannot be reached, setting a third target speed,
 determining whether the third target speed can be reached, and,
 if the third target speed can be reached, maintaining the third target speed until the set dose of medicine has been injected from the injection device.

3. The system of claim 2, wherein the control module shuts down the motor if the third target speed cannot be reached.

4. An injection device for injecting a set dose of medicine from a ampoule containing medicine, the injection device comprising a system comprising:
 an electrical motor operatively coupled to a direction sensitive encoded unit, and
 a control module, wherein the control module sets a first target speed to be reached by the piston rod prior to beginning an injection, and,
  determines whether the first target speed can be reached, and
  if the first target speed can be reached, maintaining the first target speed until the set dose of medicine has been injected from the injection device, and
 if the first target speed cannot been reached, setting a second target speed,
  determining whether the second target speed can be reached, and,
  if the second target speed can be reached, maintaining the second target speed until the set dose of medicine has been injected from the injection device, and
 if the second target speed cannot be reached, setting a third target speed.

* * * * *